(12) United States Patent
Mao et al.

(10) Patent No.: US 9,921,213 B2
(45) Date of Patent: Mar. 20, 2018

(54) RAPID DIAGNOSIS METHOD OF CITRUS HUANGLONGBING

(71) Applicant: GUANGDONG ENTOMOLOGICAL INSTITUTE, Guangzhou, Guangdong Province (CN)

(72) Inventors: Runqian Mao, Guangzhou (CN); Yuhong Zhang, Guangzhou (CN); Jihuan Zheng, Guangzhou (CN); Zhiping Pan, Guangzhou (CN); Jincheng Quan, Guangzhou (CN); Mingdu Huang, Guangzhou (CN)

(73) Assignee: GUANGDONG INSTITUTE OF APPLIED BIOLOGICAL RESOURCE, Guangzhou (CN)

( * ) Notice: Subject to any disclaimer, the term of this patent is extended or adjusted under 35 U.S.C. 154(b) by 0 days.

(21) Appl. No.: 14/898,965

(22) PCT Filed: Jul. 16, 2013

(86) PCT No.: PCT/CN2013/079470
§ 371 (c)(1),
(2) Date: Dec. 16, 2015

(87) PCT Pub. No.: WO2014/201744
PCT Pub. Date: Dec. 24, 2014

(65) Prior Publication Data
US 2016/0195517 A1    Jul. 7, 2016

(30) Foreign Application Priority Data
Jun. 19, 2013 (CN) .......................... 2013 1 0244391

(51) Int. Cl.
*G01N 33/50* (2006.01)
*G01N 21/78* (2006.01)
*G01N 33/569* (2006.01)

(52) U.S. Cl.
CPC ......... *G01N 33/5097* (2013.01); *G01N 21/78* (2013.01); *G01N 33/56961* (2013.01); *G01N 2333/43552* (2013.01)

(58) Field of Classification Search
None
See application file for complete search history.

(56) References Cited

U.S. PATENT DOCUMENTS

2013/0247451 A1* 9/2013 Vanhercke .......... C07K 14/415
44/388

FOREIGN PATENT DOCUMENTS

| CN | 102042979 A | 5/2011 |
| CN | 102586481 A | 7/2012 |
| CN | 102605092 A | 7/2012 |
| CN | 102866253 A | 1/2013 |
| CN | 103120105 A | 5/2013 |
| JP | 2004-264101 A | 9/2004 |
| JP | 2007-33353 A | 2/2007 |
| WO | 2010/069017 A1 | 6/2010 |

OTHER PUBLICATIONS

Exteberria et al., "An Iodine-Based Starch Test to Assist in Selecting Leaves for HLB Testing"; HS1122, Institute of Food and Agricultural Sciences, University of Florida: Gainesville, FL, 2007; pp. 1-5.*
International Search Report dated Mar. 27, 2014, issued in counterpart International Application No. PCT/CN2013/079470 (3 pages).
Hong et al., "Iodine Reaction Quick Detection of Huanglongbin Disease", Southern Fruit Research Institute, Dec. 31, 2003, pp. 1-11 (11 pages).

* cited by examiner

*Primary Examiner* — Michelle F. Paguio Frising
(74) *Attorney, Agent, or Firm* — Westerman, Hattori, Daniels & Adrian, LLP

(57) ABSTRACT

The present invention discloses a rapid diagnosis method of citrus huanglongbing. In the present invention, the accuracy of diagnosis of citrus huanglongbing is significantly improved in the following manners: eliminating the interference of residual starch by effectively removing the residual starch contained in the leaf; eliminating the interference of chlorophyll by effectively removing chlorophyll; and directly developing the color on the leaf rather than mixing and grinding the leaf in water, so as to avoid the problem that the accuracy of color development reaction conducted by mixing the leaf with water is liable to be interfered since the starch is insoluble in water. Therefore a rapid diagnosis of the citrus huanglongbing with much higher accuracy is achieved, which provides effective detection means for the control of the citrus huanglongbing and is beneficial for the control of the citrus huanglongbing.

4 Claims, 4 Drawing Sheets

RAPID DIAGNOSIS METHOD OF CITRUS HUANGLONGBING

FIELD OF THE INVENTION

The present invention belongs to the field of disease control of citrus, and particularly relates to a rapid diagnosis method of citrus huanglongbing.

BACKGROUND OF THE INVENTION

China is one of the largest citrus producing countries, and the citrus industry is one of the mainstay industries of agriculture in China, which occupies a very important place in the agricultural economy and plays a very crucial role in increasing farmers' income, increasing social employment and building a new socialist countryside. Diseases and insect pests of citrus are great obstacles to the development of the citrus industry, wherein the most serious one is the citrus huanglongbing which is known as a "cancer" of the citrus. With fast development of the citrus industry, the occurrence and damage of citrus huanglongbing become increasingly serious. This disease is an infectious plant disease with great harm, with a long lasting period of epidemic, a wide incidence range and a high incidence rate, which leads to a short lifetime, a low yield and a high production cost of citrus in most areas of China, and leads to an annual economic loss of up to billions of dollars, seriously impeding and restricting the development of the citrus industry in China and even around the world. Research results have proven that the huanglongbing pathogen in the field is mainly transmitted through Diaphorina citri. Therefore, for controlling the huanglongbing, it is the core issue to control Diaphorina citri and reduce the population quantity of Diaphorina citri in the field. Guangdong Entomological Institute had made a relatively thorough research in respect of the Diaphorina citri and the citrus huanglongbing, and has applied for an invention patent titled "Method for Controlling Diaphorina Citri and Citrus Huanglongbing in Citrus Orchards" with the application number of 201310049098.6.

However, the main problem for the control of the citrus huanglongbing at present is high difficulties, high technical requirements, and difficulties in implementation. The key of the problem lies in that since the detection and diagnosis technique cannot keep up, the farmers do not consider that their citrus trees have been infected with the citrus huanglongbing, and thus they take no active measures. Therefore, for the control of citrus huanglongbing, it is a technical difficulty in urgent need to develop a detection and diagnosis technique which is fast-ready and easily operated.

Currently, the detection and diagnosis technique mainly includes diagnosis of field symptoms and identification via an indicator plant, diagnosis through electron microscope detection, diagnosis through immunological detection, diagnosis through detection of nucleic acid molecules and a diagnosis method based on the starch iodine reaction (Zhang Liping, 2009), wherein the PCR technique is a mainstream technique at present (Deng Xiaoling et al., 1999; Wang Zhongkang et al., 2004; Meng Xiangchun et al., 2007). The diagnosis method based on the starch-iodine reaction was derived as follows. Schneider (1968) found that a leaf infected with the citrus huanglongbing has very high starch content, and in 2002, by using a histological method, Masatoshi Onuki proved that a large number of starch grains are accumulated in a citrus leaf infected with the citrus huanglongbing. Le Thi Thu Hong and Nguyen Thi Ngoc Truc (2003) subsequently built the technique which diagnoses the citrus huanglongbing through the iodine reaction, with the following key points: (1) collecting leaves with the features of the citrus huanglongbing in the morning, collecting no inner leaves, rolled leaves, tender leaves, branches, fruits and roots; (2) taking 1 g of leaves, mixing it with 2 ml of distilled water and grinding; (3) dropwise adding 2 μL of mixed liquor of leaves and water onto a reaction film (NCM, NitroCellulose Membrane), and after 5 minutes dropwise adding 2 μL of iodine solution onto the sample on the reaction film; and (4) observing the color change of the leaves to obtain a result, wherein if a negative reaction occurs, the color is not changed, and if a positive reaction occurs, the color is changed to blue. In Japan, TAKUSHI (2007) measured that the content of starch in the citrus leaves infected with the citrus huanglongbing is 400-500 mg/kg while the content of starch in normal leaves is 85.6 mg/kg, and built a rapid diagnosis technique. In the technique, they scratched a surface of a leaf with an abrasive paper for 20 times, subsequently put the abrasive paper into a plastic bag, and added 25 μL of iodine solution into the bag for color development. In Malaysia, Lily Eng (2007) repeated the above method by using different abrasive paper. In China, Zhang Liping et al. (2009) repeated the technique by the following steps: grinding the collected citrus material which were infected with the disease; adding an equivalent amount of pure water; then drawing 4 μL of mixed liquor of leaves and water onto the reaction film; and after 5 min, adding an equivalent amount of iodine solution and observing the color change, wherein the consistency between the experiment result and the PCR result reached 93.3%. Through researches, the inventor found that the reasons for the unwide application of starch color development technique are as follows: (1) since the sample is captured in the morning, the interference of starch in normal leaves are not truly eliminated, while sometimes due to environmental factors, starch accumulated by photosynthesis of normal leaves may not be transferred away in the evening and thus the starch remains in normal leaves in the morning; (2) since the chlorophyll is not removed by the aforementioned technique, interference of the chlorophyll exists during the color development and may affect the accuracy of detection and diagnosis; and (3) in the aforementioned diagnosis technique, the leaves need to be mixed with water for grinding, but the starch is insoluble in water, such that the accuracy of the color development reaction when the leaves are mixed with water is affected.

SUMMARY OF THE INVENTION

The aim of the present invention is to provide a rapid diagnosis method of citrus huanglongbing, which is simple and fast and has high accuracy.

The rapid diagnosis method of citrus huanglongbing of the present invention includes the following steps:

a. dark treatment: bagging a citrus leaf to be detected with a black bag, sealing the bag and conducting a dark treatment for 12-24 hours to obtain a dark-treated leaf; or collecting a citrus branch to be detected, bringing the branch indoors and inserting the branch in water, then bagging a leaf of the branch with a black bag or putting the branch in a dark room to conduct a dark treatment for 12-24 hours, and subsequently collecting the leaf to obtain a dark-treated leaf; or before sunrise, collecting an overnight citrus leaf to be detected as the dark-treated leaf;

b. freezing treatment of the leaf: clipping the dark-treated leaf, wherein the leaf is clipped at least on one side of the main vein from a side edge of the leaf along a lateral vein direction towards the main vein and until the main vein is reached, without cutting off the main vein, so as to clip the leaf into several thin strips, and then freezing the thin strips under −4 to −15° C. for 12-24 hours to obtain a frozen leaf; or freezing the dark-treated leaf under −4 to −15° C. for 12-24 hours, then clipping the leaf, wherein the leaf is clipped at least on one side of the main vein from a side edge of the leaf along a lateral vein direction towards the main vein and until the main vein is reached, without cutting off the main vein, so as to clip the leaf into several thin strips, and thereby obtaining the frozen leaf;

c. decoloration of the leaf: putting the frozen leaf into a chlorophyll decoloring solution until the thin strip of the leaf turns white, and then taking the thin strip out to obtain a decolored leaf; and d. detection through color development: dropwise adding a starch color-development solution onto the decolored thin strip of the leaf, and then observing the color change of the leaf, wherein if the leaf turns blue, it infers that the citrus leaf to be detected is a leaf infected with the citrus huanglongbing, and if the color of the leaf is not changed, the leaf is a normal one.

The chlorophyll decoloring solution refers to a solution capable of removing chlorophyll, and is preferably acetone, ethyl alcohol, benzene, methyl benzene, dimethyl benzene or other organic solvents, or a mixture thereof.

The starch color-development solution refers to a solution enabling color development of the starch, and is preferably an iodine tincture, potassium iodide solution, or polyvinylpyrrolidone-iodine.

The thin strip is preferably a thin strip with a width of 1 mm.

In the present invention, through the dark treatment, the starch contained in a normal leaf is transferred, and thus no starch is accumulated in the leaf. In contrast, for a leaf infected with the citrus huanglongbing, since the sieve tube is blocked, the starch cannot be transferred and is accumulated in the leaf, the interference of the starch contained in a normal leaf can be truly eliminated through the dark treatment and thus the accuracy is improved.

The freezing treatment of the leaf mainly aims at removing the chlorophyll, while in the prior art the chlorophyll is not completely removed and thus interference of the chlorophyll to the color development exists, which also influences the accuracy of detection and diagnosis. In the present invention, with the freezing treatment, the rupture of cell membrane is accelerated due to abrupt temperature changes, and thus the dissolving and bleaching time of chlorophyll is shortened; and furthermore the leaf is clipped into thin strips to accelerate the dissolution of chlorophyll, but the leaf is not completely cut off to keep the shape of the leaf, which facilitates subsequent steps. The aforementioned steps accelerate the dissolution of chlorophyll, and facilitate complete dissolution of chlorophyll so as to remove the chlorophyll. The decoloration process of the leaf is conducted as follows: dissolving and extracting chlorophyll contained in a leaf by a chlorophyll decoloring solution until the leaf turns white, so as to completely remove the chlorophyll and avoid any influence to the accuracy of detection and diagnosis caused by interference from the existence of chlorophyll.

The detection through color development is conducted by using the principle that a leaf infected with citrus huanglongbing is rich in starch which turns blue in the presence of iodine, while a normal leaf does not contain the starch and thus the color thereof is not changed. Therefore it can be determined whether the leaf to be detected is a leaf infected with citrus huanglongbing by performing detection and diagnosis on the aforementioned decolored leaf with a starch color-development solution.

The differences between the rapid diagnosis method of citrus huanglongbing provided by the present invention and that of the prior art are shown in table 1:

TABLE 1

| Technical content | Color development technique in the prior art | The present invention |
| --- | --- | --- |
| Grinding of leaf | Required | Not required |
| Dark treatment | No | Yes |
| Decoloration (removing the chlorophyll) | No | Yes |
| Leaf shape | Presented as a slurry after the grinding | The leaf is clipped into thin strips but the middle main vein is not cut off to keep the entire shape of the leaf |
| Condition of color development | The color development is conducted on a reaction film | The color development is conducted directly on a leaf |
| Consistency to PCR detection | 93.3% | 99.9% |

In the present invention, the accuracy of diagnosis of citrus huanglongbing is significantly improved in the following manners: eliminating the interference of residual starch by effectively removing the residual starch contained in the leaf; eliminating the interference of chlorophyll by effectively removing chlorophyll; and color development is directly conducted on the leaf rather than by mixing and grinding the leaf in water, so as to avoid the problem that the accuracy of color development reaction conducted by mixing the leaf with water is liable to be interfered since the starch is insoluble in water. Therefore a rapid diagnosis of the citrus huanglongbing with much higher accuracy is achieved, which provides effective detection means for the control of citrus huanglongbing and is beneficial for the control of citrus huanglongbing.

DETAILED DESCRIPTION OF THE EMBODIMENTS

The following embodiments are provided for further illustration of the present invention, and not for the purpose of limiting the invention.

Embodiment 1: Detection and Diagnosis of Citrus Huanglongbing in Sugar Orange

Figure 1:
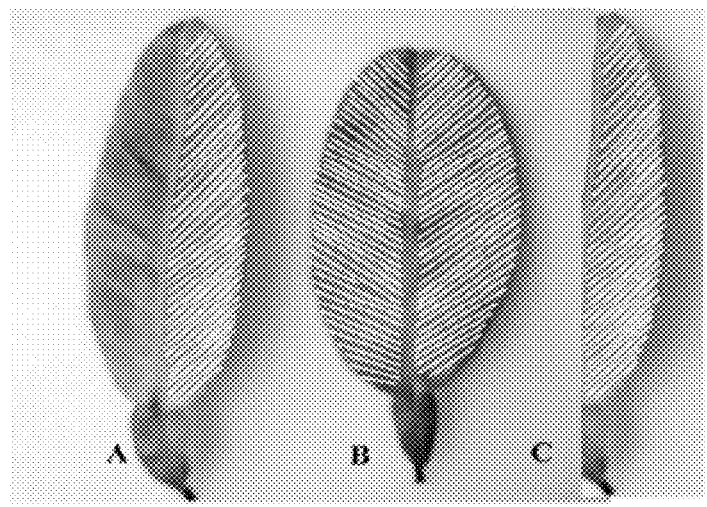
FIG. 1 is a schematic diagram of three cases in which a leaf is clipped into thin strips, wherein A represents the case that the leaf is clipped only on one side of the main vein, B represents the case that the leaf is clipped on both sides of the main vein leaf; and C represents the case that one side of the leaf is removed, and the other side is clipped.
Figure 2:
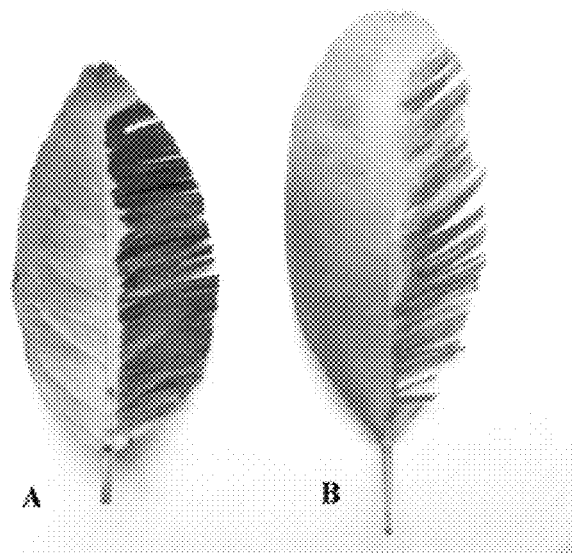
FIG. 2 is a diagram showing the diagnosis result of embodiment 1.

The embodiment is conducted in Luogang Citrus Orchard in Guangzhou. A dark treatment was performed at 10:00 on Apr. 12, 2013 [leaves of the sugar orange tree to be detected (the leaves to be detected were leaves infected with the citrus huanglongbing, as diagnosed through a detection of nucleic acid molecules) were bagged with black plastic bags, and then the bags were sealed with clamps]. At 9:30 a.m. on April 13$^{th}$, the leaves were collected as dark-treated leaves, put into the black plastic bag and brought indoors. At 4:00 p.m., the leaves were clipped into thin strips with a width of 1 mm indoors (each leaf was clipped on one side of the main vein from a side edge of the leaf along a leaf lateral vein direction towards the main vein and until the main vein was reached, without cutting off the main vein, so as to clip the leaves into several thin strips with the width of 1 mm, as shown in FIG. 1A), and then the leaves were frozen in the freezer of a refrigerator under a freezing temperature of −10° C. At 8:00 a.m. on April 14$^{th}$, the frozen leaves were taken out and transferred into test tubes, and then a chlorophyll decoloring solution (acetone) of 25 ml was added into each test tube, wherein during the adding process, the tube was shaken for 2-3 times. At 3:00 p.m. on April 14$^{th}$, the thin strips of leaves turned white, then the decoloring solution was poured out from the tube to obtain decolored leaves; and then a starch color-development solution (iodine tincture) was directly added onto the thin strips of the decolored leaves dropwise so as to perform a diagnosis by observing the color change of the leaves. The result is as shown in FIG. 2, wherein in FIG. 2, A is the leaf to be detected in this embodiment, and B is a normal leaf not infected with the citrus huanglongbing as proved by the prior art. It can be seen from FIG. 2 that after the leaf (A) to be detected in this embodiment is color-developed, the thin-strip-shaped leaf turns blue, such that the leaf (A) to be detected is determined to be a leaf infected with citrus huanglongbing; and the color of the normal leaf (B) is not changed, such that the leaf (B) is determined to be a normal leaf not infected with citrus huanglongbing. This detection result is consistent with the detection result obtained by diagnosing with a conventional detection of nucleic acid molecule.

Embodiment 2: Detection and Diagnosis of Citrus Huanglongbing in Mashui Orange

This embodiment is conducted in Yangchun Orchard. A dark treatment was performed at 3:00 p.m. [leaves of the Mashui orange to be detected (the leaves to be detected were leaves infected with citrus huanglongbing, as diagnosed through the detection of nucleic acid molecules) were bagged with black bags, and then the bags were sealed with clamps]. In the next morning, the leaves were taken out as dark-treated leaves, and then were frozen in the freezer of a refrigerator under a freezing temperature of −15° C. for 12 hours. Subsequently the leaves were clipped into thin strips with a width of 1 mm (each leaf was clipped on one side of the main vein from a side edge of the leaf along a leaf lateral vein direction towards the main vein and until the main vein was reached, without cutting off the main vein, so as to clip the leaves into several thin strips with the width of 1 mm, as shown in FIG. 1A), so as to obtain frozen leaves. The frozen leaves were decolored in a chlorophyll decoloring solution (ethyl alcohol) for 6 hours and thus the thin strips of the leaf turned white. Decolored leaves were obtained by pouring out the decoloring solution and taking the leaves out. Thereafter a starch color-development solution (potassium iodide solution) was added onto the thin strips of the decolored leaves dropwise so as to perform a diagnosis.

Figure 3:
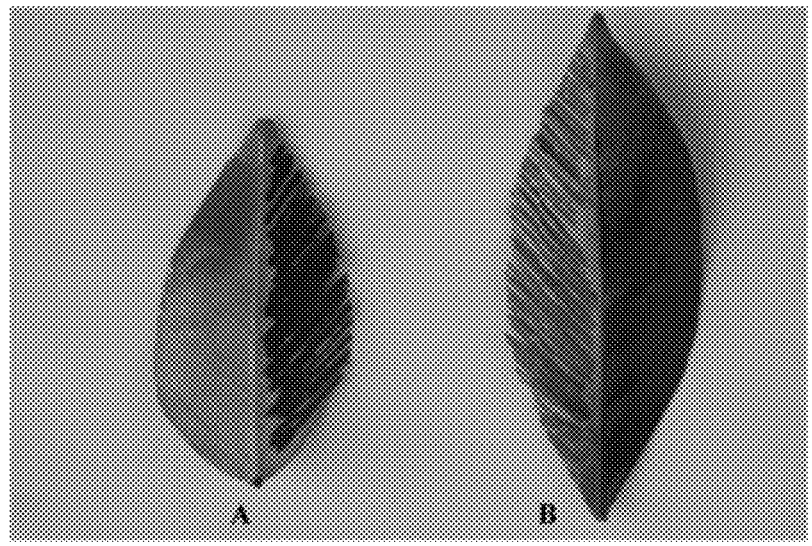
FIG. 3 is a diagram showing the diagnosis result of embodiment 2.

The result is as shown in FIG. 3, wherein in FIG. 3, A is the leaf to be detected in this embodiment, and B is a normal leaf not infected with the citrus huanglongbing as proved by the prior art. It can be seen from FIG. 3 that after the leaf (A) to be detected in this embodiment is color-developed, the thin-strip-shaped leaf turns blue such that the leaf (A) to be detected is determined to be a leaf infected with the citrus huanglongbing; and the color of the normal leaf (B) is not changed such that the leaf (B) is determined to be a normal leaf (B) not infected with citrus huanglongbing. This detection result is consistent with a detection result obtained by diagnosing with a conventional detection of nucleic acid molecule.

Embodiment 3: Detection and Diagnosis of Citrus Huanglongbing in Luogang Citrus

The embodiment is conducted in the Luogang Citrus Orchard in Luogang District, Guangzhou. A dark treatment was performed at 10:00 on Apr. 12, 2013 [leaves of the Luogang citrus tree to be detected (the leaves to be detected were leaves infected with the citrus huanglongbing, as diagnosed through detection of nucleic acid molecules) were bagged with black plastic bags, and then the bags were sealed with clamps]. At 9:30 a.m. on April 13$^{th}$, the leaves were collected as dark-treated leaves, put in the black plastic bag and brought indoors. At 4:00 p.m. on April 13$^{th}$, the dark-treated leaves were clipped indoors into thin strips with a width of 1 mm (each leaf was clipped on one side of the main vein from a side edge of the leaf along a leaf lateral vein direction towards the main vein and until the main vein was reached, without cutting off the main vein, so as to clip the leaves into several thin strips with the width of 1 mm, as shown in FIG. 1A), and then were frozen in the freezer of a refrigerator under a freezing temperature of −4° C. At 8:00 a.m. on April 14$^{th}$, the frozen leaves were taken out and transferred into test tubes, and then a chlorophyll decoloring solution (acetone) of 25 ml was added into each test tube, wherein during the addition, the tube was shaken for 2-3 times. At 3:00 p.m. on April 14$^{th}$, the thin strips of leaves turned white, then the decoloring solution was poured out from the tube to obtain decolored leaves; and then a starch color-development solution (iodine tincture) was directly added onto the thin strips of the decolored leaves dropwise so as to perform a diagnosis by observing the color change of the leaves.

Figure 4:
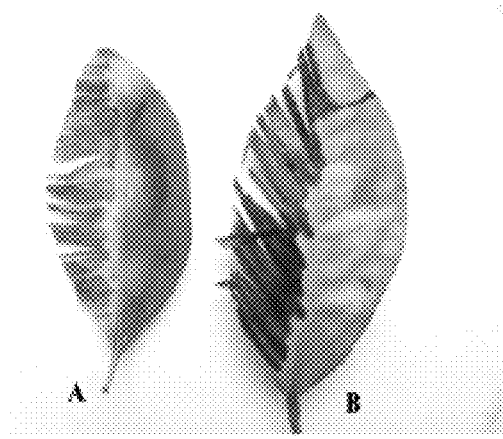
FIG. 4 is a diagram showing the diagnosis result of embodiment 3.

The result is as shown in FIG. 4, wherein in FIG. 4, B is the leaf to be detected in this embodiment, and A is a normal leaf not infected with the citrus huanglongbing as proved by the prior art. It can be seen from FIG. 4 that after the leaf (B) to be detected in this embodiment is color-developed, the thin-strip-shaped leaf turns blue, such that the leaf (B) to be detected is determined to be a leaf infected with the citrus huanglongbing; and the color of the normal leaf (A) is not changed, such that the leaf (A) is determined to be a normal leaf (A) not infected with the citrus huanglongbing. This detection result is consistent with a detection result obtained by diagnosing with a conventional detection of nucleic acid molecule.

Embodiment 4: Detection and Diagnosis of Citrus Huanglongbing in Navel Orange

The embodiment is conducted in the orchard of Atoca Orange Limited located in Lechang, Shaoguan from May 15$^{th}$ to 17$^{th}$ in 2013. A dark treatment was performed at 5:00 p.m. on May 15$^{th}$ (leaves of the navel orange to be detected were bagged with black plastic bags, and then the bags were sealed with clamps). At 6:00 a.m. on May 16$^{th}$, the leaves (the leaves to be detected were leaves infected with the citrus huanglongbing, as diagnosed through detection of nucleic acid molecules) were collected as dark-treated leaves and brought indoors (the sampling cite was about 100 M away from indoor). Subsequently the leaves were frozen in the freezer of a refrigerator under a freezing temperature of −4° C. for 24 hours, and then clipped into thin strips with a width of 1 mm (each leaf was clipped on one side of the main vein from a side edge of the leaf along a leaf lateral vein direction towards the main vein and until the main vein was reached, without cutting off the main vein, so as to clip the leaves into several thin strips with the width of 1 mm, as shown in FIG. 1A), so as to obtain frozen leaves. The frozen leaves were transferred into test tube, and then a chlorophyll decoloring solution (methyl benzene) of 25 ml was added into each test tube, wherein during the addition, the tube was shaken for 2-3 times. After 10 hours, the thin-strip-shaped leaves turned white. Thereafter decolored leaves were obtained by pouring out the decoloring solution and taking the leaves out. Then a starch color-development solution (iodine tincture) was directly added onto the thin strips of the decolored leaves dropwise so as to perform a diagnosis by observing the color change of the leaves.

Figure 5:
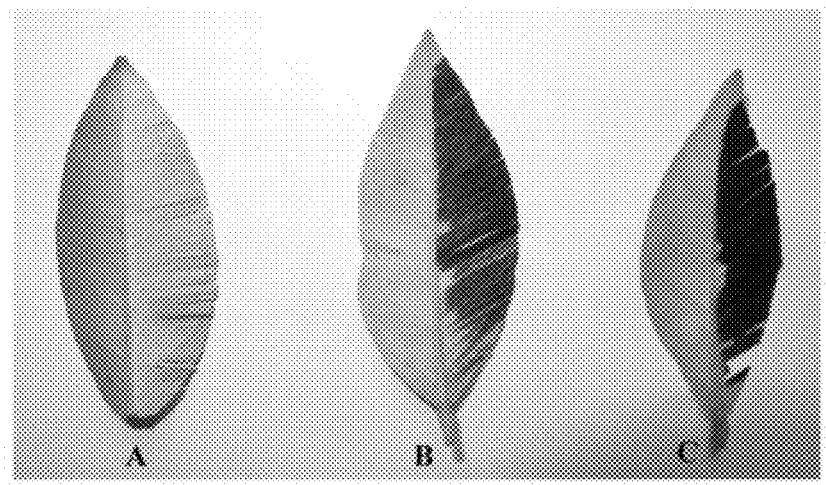
FIG. 5 is a diagram showing the diagnosis result of embodiment 4.

The result is as shown in FIG. 5, wherein in FIGS. 5, B and C are leaves to be detected in this embodiment, and A is a normal leaf not infected with the citrus huanglongbing as proved by the prior art. It can be seen from FIG. 5 that after the leaves (B and C) to be detected in this embodiment are color-developed, the thin-strip-shaped leaves turn blue, such that the leaves (B and C) to be detected are determined to be leaves infected with the citrus huanglongbing; and the color of the normal leaf (A) is not changed, such that the leaf (A) is determined to be a normal leaf not infected with the citrus huanglongbing. This detection result is consistent with a detection result obtained by diagnosing with a conventional detection of nucleic acid molecule.

Embodiment 5: Detection and Diagnosis of Citrus Huanglongbing in Hongjiang Orange The embodiment is conducted in Qingping Orchard located in Lianjiang. At 1:00 p.m. on May 23, 2013, a branch of Hongjiang orange to be detected was collected and brought indoors. The branch was inserted in water and then stayed in a dark room. At 8:00 a.m. on May 24$^{th}$, leaves were collected from the branch as dark-treated leaves. Subsequently the leaves were frozen in the freezer of a refrigerator under a freezing temperature of −4° C. for 24 hours, and then clipped into thin strips with a width of 1 mm (each leaf was clipped on one side of the main vein from a side edge of the leaf along a leaf lateral vein direction towards the main vein and until the main vein was reached, without cutting off the main vein, so as to clip the leaves into several thin strips with the width of 1 mm, as shown in FIG. 1A), so as to obtain frozen leaves. The frozen leaves were transferred into test tubes, and then a chlorophyll decoloring solution (methyl benzene) of 25 ml was added into each tube, wherein during the addition, the tube was shaken for 2-3 times. After 6 hours, the thin-strip-shaped leaves turned white. Thereafter the decoloring solution was poured out, and a starch color-development solution (iodine tincture) was added dropwise so as to perform a diagnosis by observing the color change of the leaves.

Figure 6:
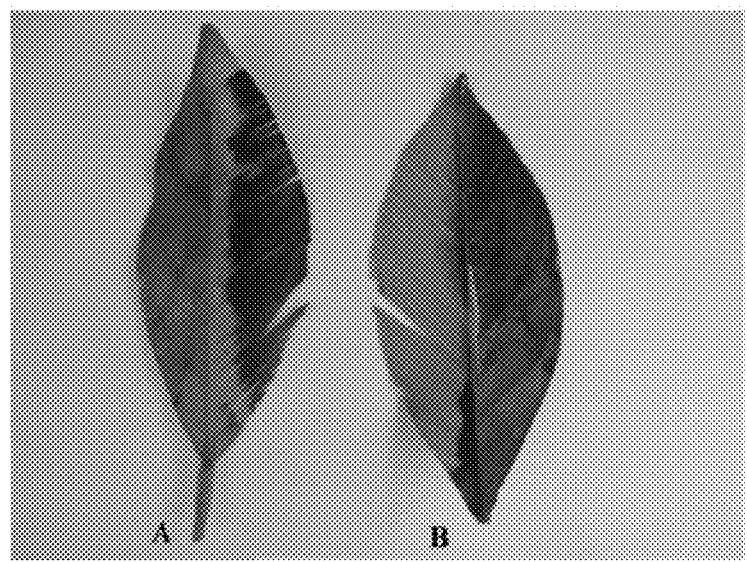
FIG. 6 is a diagram showing the diagnosis result of embodiment 5.

The result is as shown in FIG. 6, wherein in FIG. 6, A is the leaf to be detected in this embodiment, and B is a normal leaf not infected with the citrus huanglongbing as proved by the prior art. It can be seen from FIG. 6 that after the leaf (A) to be detected in this embodiment is color-developed, the thin-strip-shaped leaf turns blue, such that the leaf (A) to be detected is determined as a leaf infected with the citrus huanglongbing; and the color of the normal leaf (B) is not changed such that the leaf is determined to be a normal leaf not infected with the citrus huanglongbing. This detection result is consistent with a detection result obtained by diagnosing with a conventional detection of nucleic acid molecule.

Embodiment 6: Detection and Diagnosis of Citrus Huanglongbing in Summer Orange

The samples are taken from the summer orange orchard in Beihai. A dark treatment was performed in the afternoon on May 25, 2013 (leaves of the summer orange to be detected were bagged with black plastic bags, and then the bags were sealed with clamps). At 7:00 a.m. on May 26$^{th}$, the dark-treated leaves (the leaves to be detected were leaves infected with the citrus huanglongbing, as diagnosed through detection of nucleic acid molecules) were collected. Subsequently the leaves were frozen in the freezer of a refrigerator under a freezing temperature of −12° C. The leaves were taken out at 6:00 a.m. on May 27$^{th}$ and then clipped into thin strips with a width of 1 mm (each leaf was clipped on one side of the main vein from a side edge of the leaf along a leaf lateral vein direction towards the main vein and until the main vein was reached, without cutting off the main vein, so as to clip the leaves into several thin strips with the width of 1 mm, as shown in FIG. 1A), so as to obtain frozen leaves. The frozen leaves were transferred into test tubes, and then a chlorophyll decoloring solution (methyl benzene) of 25 ml was added into each test tube, wherein during the addition, the tube was shaken for 2-3 times. At twelve in the noon, the thin-strip-shaped leaves turned white. Thereafter a starch color-development solution (iodine tincture) was directly added onto the thin strips of the decolored leaves dropwise, so as to perform a diagnosis by observing the color change of the leaves.

Figure 7:
FIG. 7 is a diagram showing the diagnosis result of embodiment 6.

The result is as shown in FIG. 7, wherein in FIG. 7, A is the leaf to be detected in this embodiment, and B is a normal leaf not infected with the citrus huanglongbing as proved by the prior art. It can be seen from FIG. 7 that after the leaf (A) to be detected in this embodiment is color-developed, the thin-strip-shaped leaf turns blue, such that the leaf to be detected is determined to be a leaf infected with the citrus huanglongbing; and the color of the normal leaf (B) is not changed, such that the leaf is determined to be a normal leaf not infected with the citrus huanglongbing. This detection result is consistent with a detection result obtained by diagnosing with a conventional detection of nucleic acid molecule.

Embodiment 7: Detection and Diagnosis of Citrus Huanglongbing in Citrus Gonggan

Figure 8:
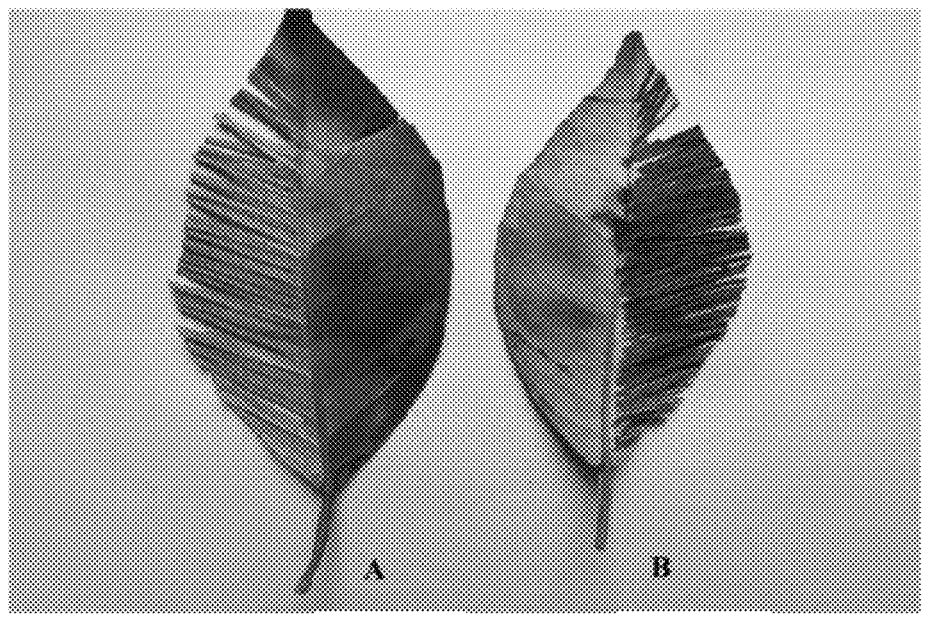
FIG. 8 is a diagram showing the diagnosis result of embodiment 7.

A branch of Citrus Gonggan to be detected was collected from the citrus orchard in Deqing on May 29, 2013 and brought indoors. The branch was inserted in water and then its leaves were bagged with black bags for a dark treatment of 24 hours, so as to obtain dark-treated leaves (the leaves to be detected were leaves infected with the citrus huanglongbing, as diagnosed through detection of nucleic acid molecules). Subsequently at 6:00 p.m. on May 30$^{th}$, the dark-treated leaves were frozen in the freezer of a refrigerator under a freezing temperature of −10° C. for 14 hours, and then at 8:00 a.m. on May 31$^{th}$, the leaves were clipped into thin strips with a width of 1 mm (each leaf was clipped on one side of the main vein from a side edge of the leaf along a leaf lateral vein direction towards the main vein and until the main vein was reached, without cutting off the main vein, so as to clip the leaves into several thin strips with the width of 1 mm, as shown in FIG. 1A), so as to obtain frozen leaves. The frozen leaves were transferred into test tubes, and then a chlorophyll decoloring solution (methyl benzene) of 25 ml was added into each test tube, wherein during the addition, the tube was shaken for 2-3 times. At 3:00 p.m., the thin strips of leaves turned white and thus decolored leaves were obtained. Then a starch color-development solution (iodine tincture) was directly added onto the thin strips of the decolored leaves dropwise, so as to perform a diagnosis by observing the color change of the leaves. The result is as shown in FIG. 8, wherein in FIG. 8, B is the leaf to be detected in this embodiment, and A is a normal leaf not infected with the citrus huanglongbing as proved by the prior art. It can be seen from FIG. 8 that after the leaf (B) to be detected in this embodiment is color-developed, the thin-strip-shaped leaf turns blue, such that the leaf to be detected is determined to be a leaf infected with the citrus huanglongbing; and the color of the normal leaf (A) is not changed, such that the leaf (A) is determined to be a normal leaf not infected with the citrus huanglongbing. This detection result is consistent with a detection result obtained by diagnosing with a conventional detection of nucleic acid molecule.

The invention claimed is:

1. A rapid diagnosis method of citrus huanglongbing, wherein the method comprises the following steps:
   a. conducting a dark treatment comprising;
      (a1) bagging a citrus leaf with a black bag, and sealing the black bag for 12-24 hours to obtain a dark-treated citrus leaf;
      (a2) collecting a citrus branch, bringing the citrus branch indoors and inserting the citrus branch into water, then bagging a citrus leaf of the citrus branch with a black bag, or placing the citrus branch in a dark room, for 12-24 hours, to obtain a dark-treated citrus leaf; or
      (a3) before sunrise, collecting an overnight citrus leaf as the dark-treated citrus leaf;
   b. a freezing treatment of the dark-treated citrus leaf comprising;
      (b1) clipping the dark-treated citrus leaf, wherein the dark-treated citrus leaf is clipped at least on one side of a main vein from a side edge of the dark-treated citrus leaf along a lateral vein direction towards the main vein and until the main vein is reached, without cutting off the main vein, so as to clip the dark-treated citrus leaf into several thin strips, and then freezing the thin strips under −4 to −15° C. for 12-24 hours to obtain a frozen citrus leaf; or
      (b2) freezing the dark-treated citrus leaf under −4 to −15° C. for 12-24 hours, then clipping the citrus leaf, wherein the citrus leaf is clipped at least on one side of a main vein from a side edge of the citrus leaf along a citrus leaf lateral vein direction towards the main vein and until the main vein is reached, without cutting off the main vein, so as to clip the citrus leaf into several thin strips, and thereby obtaining the frozen citrus leaf;
   c. a decoloration step comprising putting the frozen citrus leaf into a chlorophyll decoloring solution until the thin strips of the citrus leaf turn white, and then removing the citrus leaf from the chlorophyll decloring solution to obtain decolored thin strips of the citrus leaf;
   d. a detection step through color development comprising adding a starch color-development solution dropwise onto the decolored thin strips of the citrus leaf, and then observing the color change of the citrus leaf, wherein the citrus leaf turning blue indicates that the citrus leaf is infected with the citrus huanglongbing, and if the color of the citrus leaf is not changed, the citrus leaf is a normal citrus leaf.

2. The rapid diagnosis method of citrus huanglongbing of claim 1, wherein the chlorophyll decoloring solution is acetone, ethyl alcohol, benzene, methyl benzene or dimethyl benzene, or a mixture thereof.

3. The rapid diagnosis method of citrus huanglongbing of claim 1, wherein the starch color-development solution is an iodine tincture, potassium iodide solution, or polyvinylpyrrolidone-iodine.

4. The rapid diagnosis method of citrus huanglongbing of claim 1, wherein the thin strips are thin strips with a width of 1 mm.

\* \* \* \* \*

UNITED STATES PATENT AND TRADEMARK OFFICE
CERTIFICATE OF CORRECTION

PATENT NO. : 9,921,213 B2
APPLICATION NO. : 14/898965
DATED : March 20, 2018
INVENTOR(S) : Runqian Mao et al.

Page 1 of 1

It is certified that error appears in the above-identified patent and that said Letters Patent is hereby corrected as shown below:

On the Title Page

Item (73):
Change:
(73) Assignee: GUANGDONG INSTITUTE OF APPLIED BIOLOGICAL RESOURCE To be:
(73) Assignee: GUANGDONG INSTITUTE OF APPLIED BIOLOGICAL RESOURCES Signed and Sealed this
Nineteenth Day of June, 2018

Andrei Iancu
*Director of the United States Patent and Trademark Office*